United States Patent
Nakagami et al.

(10) Patent No.: US 10,918,585 B2
(45) Date of Patent: Feb. 16, 2021

(54) ANTI-AGING AGENT AND ANTI-AGING COMPOSITION FOR SKIN

(71) Applicant: SHOWA DENKO K.K., Tokyo (JP)

(72) Inventors: Yuko Nakagami, Fujisawa (JP); Shinji Yamaki, Kawasaki (JP); Ichiro Fujita, Kawasaki (JP); Tadashi Yoneda, Chiba (JP)

(73) Assignee: SHOWA DENKO K.K., Tokyo (JP)

( * ) Notice: Subject to any disclaimer, the term of this patent is extended or adjusted under 35 U.S.C. 154(b) by 0 days.

(21) Appl. No.: 16/061,008

(22) PCT Filed: Oct. 28, 2016

(86) PCT No.: PCT/JP2016/082117
§ 371 (c)(1),
(2) Date: Jun. 11, 2018

(87) PCT Pub. No.: WO2017/110248
PCT Pub. Date: Jun. 29, 2017

(65) Prior Publication Data
US 2018/0360719 A1    Dec. 20, 2018

(30) Foreign Application Priority Data

Dec. 22, 2015 (JP) .............................. JP2015-250071

(51) Int. Cl.
| | | |
|---|---|---|
| A61K 8/60 | (2006.01) | |
| A61Q 19/08 | (2006.01) | |
| A61P 43/00 | (2006.01) | |
| A61K 31/7034 | (2006.01) | |
| A61K 8/73 | (2006.01) | |
| A61K 31/7016 | (2006.01) | |
| A61K 31/702 | (2006.01) | |

(52) U.S. Cl.
CPC .................. *A61K 8/60* (2013.01); *A61K 8/73* (2013.01); *A61K 31/702* (2013.01); *A61K 31/7016* (2013.01); *A61K 31/7034* (2013.01); *A61P 43/00* (2018.01); *A61Q 19/08* (2013.01)

(58) Field of Classification Search
CPC .......... A61K 8/60; A61K 8/73; A61K 31/702; A61K 31/7016; A61Q 19/08
USPC ....................................................... 514/53
See application file for complete search history.

(56) References Cited

U.S. PATENT DOCUMENTS

| | | |
|---|---|---|
| 2007/0219158 A1 | 9/2007 | Aoki et al. |
| 2012/0121534 A1 | 5/2012 | Thorel et al. |

FOREIGN PATENT DOCUMENTS

| | | |
|---|---|---|
| DE | 19624705 A1 | 1/1998 |
| EP | 3213753 A1 | 9/2017 |
| EP | 3219304 A1 | 9/2017 |
| FR | 2948286 A1 | 1/2011 |
| JP | 2005-306867 A | 11/2005 |
| JP | 2005306867 A * | 11/2005 |
| JP | 2007-084484 A | 4/2007 |
| JP | 2007084484 A * | 4/2007 |
| JP | 2008-239533 A | 10/2008 |
| JP | 2008239533 A * | 10/2008 |
| JP | 5722030 B2 | 5/2015 |
| WO | 2005092285 A1 | 10/2005 |
| WO | 2015178385 A1 | 11/2015 |

OTHER PUBLICATIONS

Aoki et al.; JP 2005306867 A; Nov. 4, 2005 (Machine English Translation).*
Okamoto et al.; JP 2008239533 A; Oct. 9, 2008 (Machine English Translation).*
Kobayashi et al.; JP 2007084484 A; Apr. 5, 2007 (Machine-English Translation).*
Laure Rittie et al., "UV-light-induced signal cascades and skin aging", Ageing Research Reviews 1, 2002, pp. 705-720.
Naoko Tsuji et al., "The Role of Elastases Secreted by Fibroblasts in Wrinkle Formation: Implication Through Selective Inhibition of Elastase Activity", Photochemistry and Photobiology, 2001, pp. 283-290, vol. 74, No. 2.
Genji Imokawa et al., "Analysis of etiologic factors involved in stratum corneum function in fine wrinkle formation and its prevention", Fragrance Journal, 1992, 16 pages, vol. 11.
International Search Report for PCT/JP2016/082117 dated Dec. 6, 2016 [PCT/ISA/210].
Kemp, J., et al., "Cyclitol Glucosides and their Role in the Synthesis of a Glucan from Uridine Diphosphate Glucose in *Phaseolus aureus*", Biochem. J., 1974, vol. 142, pp. 153-159 (8 pages).
Communication dated Jul. 16, 2019 from the European Patent Office in application No. 16878146.6.
Notification of Reasons for Rejection dated Sep. 1, 2020 from the Japanese Patent Office in application No. 2017-557765.

* cited by examiner

*Primary Examiner* — Shaojia A Jiang
*Assistant Examiner* — Michael C Henry
(74) *Attorney, Agent, or Firm* — Sughrue Mion, PLLC

(57) ABSTRACT

Provided is an anti-aging agent for skin which contains, as an active component, an inositol derivative in which a monosaccharide or an oligosaccharide is bonded to inositol, in which a total amount of the monosaccharide or the oligosaccharide bonded to one inositol molecule is 2 or greater in terms of monosaccharide unit.

8 Claims, No Drawings

ANTI-AGING AGENT AND ANTI-AGING COMPOSITION FOR SKIN

CROSS REFERENCE TO RELATED APPLICATIONS

This application is a National Stage of International Application No. PCT/JP2016/082117 filed Oct. 28, 2016, claiming priority based on Japanese Patent Application No. 2015-250071 filed Dec. 22, 2015, the content of which is incorporated herein by reference.

TECHNICAL FIELD

The present invention relates to an anti-aging agent and an anti-aging composition for skin.

BACKGROUND ART

The skin is exposed to various external stimuli such as ultraviolet rays. As a result, functional degradation of the skin is caused such that various aging phenomena of the skin become significant. Wrinkles generated, as an aging phenomenon of skin, are mainly classified into epidermal wrinkles caused by dryness and dermal wrinkles caused by prolonged exposure to ultraviolet rays.

The epidermal wrinkles indicate relatively shallow wrinkles generated at the outer corners of the eyes and the mouth, and it has been reported that the wrinkle area ratio is high in people with skin conditions having low moisture content in the stratum corneum(for example, see NPL 3). It has been known that fine wrinkles are worsened by rough skin or dry skin.

Meanwhile, as the mechanism of forming dermal wrinkles, degradation of the ability of synthesizing collagen and elastin in dermal fibroblasts due to ultraviolet rays; and promotion of decomposition of matrix components due to an increase in matrix metalloprotease and elastase which are collagenolytic enzymes (for example, see NPLs 1 and 2) are exemplified.

In the related art, as an anti-aging agent for skin that prevents and improves epidermal wrinkles, various humectants or agents for suppressing reduction of the moisture content in the horny layer have been developed (for example, see PTL 1). In addition, as an anti-aging agent for skin that prevents and improves dermal wrinkles, for example, vitamin Cs, vitamin As, low molecular collagen, amino acids, and plant extracts which exhibit an action of promoting dermal matrix component production have been used.

CITATION LIST

Patent Literature

[PTL 1] Japanese Patent No. 5722030 Non-Patent Literature

[NPL 1] Rittie L. and Fisher G. J., UV-light-induced signal cascades and skin aging., Ageing Res. Rev., 1 (4), 705-720, 2002.

[NPL 2] Tsuji N., et al., The role of elastases secreted by fibroblasts in wrinkle formation: implication through selective inhibition of elastase activity., Photochem. Photobiol., 74 (2), 283-290, 2001.

[NPL 3] Imokawa et al., "Generation Factors and Prevention of Fine Wrinkles Involving Epidermis, Particularly Stratum Corneum", Fragrance Journal, (11), 29 to 42, 1992.

SUMMARY OF INVENTION

Technical Problem

However, anti-aging agents for skin of the related art do not sufficiently exert effects of preventing and improving wrinkles in some cases. Further, for the purpose of preventing and improving epidermal wrinkles and dermal wrinkles at the same time, different chemical agents that respectively exert an effect on epidermal wrinkles and on dermal wrinkles have been used in combination in most cases, and chemical agents that exert effects on both epidermal wrinkles and dermal wrinkle have not been known. Therefore, an object of the present invention is to provide an anti-aging agent for skin that exerts effects on both epidermal wrinkles and dermal wrinkles.

Solution to Problem

The present invention includes the following aspects.

(1) An anti-aging agent for skin comprising, as an active component: an inositol derivative in which a monosaccharide or an oligosaccharide is bonded to inositol, in which a total amount of the monosaccharide or the oligosaccharide bonded to one inositol molecule is 2 or greater in terms of monosaccharide unit.

(2) The anti-aging agent for skin according to (1) which is used for promoting production of collagen.

(3) The anti-aging agent for skin according to (1) or (2) which is used for promoting production of elastin.

(4) The anti-aging agent for skin according to any one of (1) to (3), in which the monosaccharide is glucose.

(5) The anti-aging agent for skin according to any one of (1) to (4), in which the oligosaccharide comprises glucose as a constituent unit.

(6) The anti-aging agent for skin according to any one of (1) to (5), in which the inositol is myo-inositol.

(7) An anti-aging composition for skin comprising: the anti-aging agent for skin according to any one of (1) to (6); and a pharmaceutically acceptable carrier.

(8) The anti-aging composition for skin according to (7), in which a content of the anti-aging agent for skin is in a range of 0.01% to 50% by mass.

(9) The anti-aging composition for skin according to (7) or (8) which is a skin external agent.

(10) The anti-aging composition for skin according to any one of (7) to (9) which is a cosmetic.

Advantageous Effects of Invention

According to the present invention, it is possible to provide an anti-aging agent for skin that exerts effects on both epidermal wrinkles and dermal wrinkles.

Description of Embodiments

[Anti-Aging Agent]

According to an embodiment of the present invention, there is provided an anti-aging agent for skin comprising, as an active component, an inositol derivative in which a monosaccharide or an oligosaccharide is bonded to inositol, and in which the total amount of the monosaccharide or the oligosaccharide bonded to one inositol molecule is 2 or greater in terms of monosaccharide unit. As described in the examples below, the anti-aging agent of the present embodiment can exert effects on both epidermal wrinkles and dermal wrinkles.

In the present specification, the monosaccharide indicates saccharides that are not further hydrolyzed and also indicate a compound serving as a constituent element at the time of forming a polysaccharide. The monosaccharide can be a minimum constituent unit of saccharides. Further, in the present specification, the "monosaccharide unit" indicates a chemical structure corresponding to a monosaccharide. The "monosaccharide unit" can be a chemical structure derived from a monosaccharide. For example, a disaccharide is two when converted into the monosaccharide unit and a trisaccharide is 3 when converted into the monosaccharide unit. More specifically, mannitol, sorbitol, xylitol, erythritol, pentaerythritol, glucose, fructose, or xylose is 1 when converted into the monosaccharide unit. Further, maltitol, sucrose, lactose, maltose, or trehalose is 2 when converted into the monosaccharide unit. Further, for example, α-cyclodextrin is 6 when converted into the monosaccharide unit, β-cyclodextrin is 7 when converted into the monosaccharide unit, and γ-cyclodextrin is 8 when converted into the monosaccharide unit.

As described in the examples below, the anti-aging agent of the present embodiment promotes expression of collagen genes and elastin genes in human fibroblasts. Therefore, the anti-aging agent of the present embodiment can be an agent for promoting production of collagen. Alternatively, the anti-aging agent of the present embodiment can be a promotor for production of collagen or a promotor for expression of collagen genes. In addition, the anti-aging agent of the present embodiment can be an agent for promoting production of elastin. Alternatively, the anti-aging agent of the present embodiment can be a promotor for production of elastin or a promotor for expression of elastin genes.

The anti-aging agent of the present embodiment exerts effects of suppressing a decrease in collagen and elastin in the skin dermis due to aging which is the factor of dermal wrinkles on the skin, improving the function of the skin dermis, and keeping the skin healthy. Further, as described in the examples below, the anti-aging agent of the present embodiment exerts the effect of improving epidermal wrinkles caused by dryness. Therefore, the anti-aging agent of the present embodiment can be an anti-wrinkle agent or a preventive or therapeutic agent for wrinkles.

An anti-aging agent of the present embodiment may be used for medical applications or non-medical applications such as cosmetics.

(Inositol Derivative)

In the anti-aging agent of the present embodiment, the inositol derivative is one in which a saccharide is bonded to inositol. As described below, the saccharide bonded to inositol may be a monosaccharide or an oligosaccharide. For example, a plurality of monosaccharides may be bonded to one inositol molecule, one or a plurality of oligosaccharides may be bonded to one inositol molecule, or one or a plurality of monosaccharides and one or a plurality of oligosaccharides may be bonded to one inositol molecule. In the inositol derivative, the total amount of the monosaccharide or the oligosaccharide bonded to one inositol molecule is 2 or greater in terms of monosaccharide unit. For example, the total amount thereof may be 3 or greater or 4 or greater.

Inositol indicates cyclic hexahydric alcohol represented by $C_6H_6(OH)_6$. There are nine stereoisomers of inositol, which are cis-inositol, epi-inositol, allo-inositol, myo-inositol, muco-inositol, neo-inositol, chiro-inositol (there is a D form and an L form), and scyllo-inositol.

In the anti-aging agent of the present embodiment, it is preferable that the inositol constituting the inositol derivative is myo-inositol which is the only inositol having physiological activity from among the above-described isomers. The inositol can be synthesized according to a method of extracting rice bran, a chemical synthesis method, or a fermentation method.

In the anti-aging agent of the present embodiment, the inositol derivative is a compound in which a saccharide is bonded to a hydroxyl group of inositol. The saccharide is bonded to any one or more hydroxyl groups from among six hydroxyl groups present in an inositol molecule.

The saccharide constituting the inositol derivative is not particularly limited, and examples thereof include mannitol, sorbitol, xylitol, maltitol, erythritol, pentaerythritol, glucose, sucrose, fructose, lactose, maltose, xylose, trehalose, α-cyclodextrin, β-cyclodextrin, and γ-cyclodextrin.

The saccharide constituting the inositol derivative may be glucose or an oligosaccharide containing glucose as a constituent unit. The oligosaccharide may contain only glucose as a constituent unit. Alternatively, the oligosaccharide may contain at least one glucose molecule and a saccharide other than glucose as a constituent unit. The molecular weight of the above-described oligosaccharide may be approximately 300 to 3000. More specific examples of the oligosaccharide include disaccharides such as sucrose, lactose, maltose, trehalose, and cellobiose; trisaccharides such as raffinose, melezitose, and maltotriose; and tetrasaccharides such as stachyose.

From the viewpoint of easily obtaining an inositol derivative with a high degree of purification, it is preferable to use β-cyclodextrin, which is industrially inexpensive and can be stably supplied, as a raw ingredient of the inositol derivative. In this case, the saccharide constituting the inositol derivative contains glucose as a constituent unit. Meanwhile, in a case where cheaper starch or the like is used as a raw ingredient of the inositol derivative, the degree of purification of the inositol derivative to be obtained tends to be unstable, since various saccharides are transferred to various places at the time of synthesis of the inositol derivative.

(Method of Synthesizing Inositol Derivative)

As a method of synthesizing an inositol derivative is not particularly limited, and an inositol derivative can be appropriately synthesized according to a known method of the related art. For example, an inositol derivative may be synthesized by reacting inositol with cyclodextrin, which is a type of oligosaccharide, in the presence of cyclodextrin glucanotransferase (for example, see Japanese Unexamined Patent Application, First Publication No. S63-196596). Alternatively, an inositol derivative may be synthesized according to a method of obtaining a glucosyl form by using glucosyl phosphite as a sugar donor (for example, see Japanese Unexamined Patent Application, First Publication No. H06-298783).

[Anti-Aging Composition]

According to an embodiment of the present invention, there is provided an anti-aging composition for skin which contains the above-described anti-aging agent and a pharmaceutically acceptable carrier. The anti-aging composition of the present embodiment may serve as a skin external agent or a cosmetic.

The anti-aging composition can be produced by mixing the above-described anti-aging agent, a pharmaceutically acceptable carrier, and other additives as necessary for formulation according to a method of the related art (for example, a method described in the Japanese pharmacopoeia).

The pharmaceutically acceptable carrier is not particularly limited, and examples thereof include an excipient, a binder, a disintegrant, a lubricant, an emulsifier, a stabilizer, a diluent, a thickener, a wetting agent, a pH regulator, an oil agent, and a solvent for an injection.

Other agents described above are not particularly limited, and examples thereof include a humectant, a touch improver, a surfactant, a polymer compound, a thickening and gelling agent, a solvent, a propellant, an antioxidant, a reducing agent, an oxidant, a preservative, an antimicrobe agent, a chelating agent, a pH regulator, an acid, an alkali, powder, an inorganic salt, an ultraviolet absorbing agent, a whitening agent, vitamins and derivatives thereof, an antiphlogistic agent, an anti-inflammatory agent, a chemical agent for hair growth, a blood circulation promotor, a stimulant, hormones, an anti-wrinkle agent, an anti-aging agent, a tightening agent, a cooling sensation agent, a warming sensation agent, a wound healing promotor, a stimulation alleviating agent, an analgesic agent, a cell activator, extracts from plants, animals, and microorganisms, an antipruritic agent, a keratin releasing and dissolving agent, an antiperspirant, a refreshing agent, an astringent agent, an enzyme, a nucleic acid, a flavoring agent, coloring matter, a colorant, a dye, a pigment, water, a metal-containing compound, an unsaturated monomer, polyvalent alcohol, a polymer additive, an antiphlogistic analgesic, an antifungal agent, an antihistamine, a sedative hypnotic, a tranquilizer, an antihypertensive agent, a hypotensive diuretic, an antibiotic, an anesthetic, an antimicrobial substance, an antiepileptic, a coronary vasodilator, a crude drug, an adjuvant, a wetting agent, an astringent agent, a thickener, a tackifier, an antipruritic agent, a keratolytic releasing agent, an ultraviolet blocker, a preservative fungicide, and a metal soap.

As the pharmaceutically acceptable carrier and other additives, typical ingredients described in the Japanese Pharmacopoeia Sixteenth Edition; Japanese Standards of Cosmetic Ingredients second edition commentary (edited by Pharmaceutical and Medical Device Regulatory Science Society of Japan, published by YAKUJI NIPPO LTD., 1984); The Japanese Cosmetic Ingredients Codex (supervised by Pharmaceutical Affairs Bureau, Evaluation Division, published by YAKUJI NIPPO, LTD., 1993); Supplement To The Japanese Cosmetic Ingredients Codex (supervised by Pharmaceutical Affairs Bureau, Evaluation Division, published by YAKUJI NIPPO, LTD., 1993); The Comprehensive Licensing Standards of Cosmetics by Category (supervised by Pharmaceutical Affairs Bureau, Evaluation Division, published by YAKUJI NIPPO, LTD., 1993); Cosmetic Ingredients Dictionary (published by Nikko Chemicals Co., Ltd, 1991); and International Cosmetic Ingredient Dictionary and Handbook 2002 Ninth Edition Vol. 1 to 4, by CTFA. More specific examples thereof include various ingredients described in Japanese Unexamined Patent Application, First Publication No. 2014-114289.

Examples of the dosage form of the anti-aging composition include dosage forms to be orally administered such as a tablet, a coated tablet, a pill, powder, a granule, a capsule, a liquid, a suspension, and an emulsion; and dosage forms to be parenterally administered such as an injection, a suppository, and a skin external agent.

More specific examples of the skin external agent include dosage forms such as a cream, a lotion, a toner, an emulsion, a foundation, a pack agent, a foam agent, a skin cleanser, an extract agent, a plaster, an ointment, a spirit, a suspending agent, a tincture, a poultice, a liniment, and an aerosol.

In the anti-aging composition of the present embodiment, one selected from the above-described inositol derivative, a salt of the inositol derivative, and solvate of these may be used alone or a combination of two or more of these may be used as the anti-aging agent. The proportion of the inositol derivative in which saccharides of two or more monosaccharide units are bonded to one inositol molecule, among all inositol derivatives contained in the anti-aging composition of the present embodiment, may be 20% by mass or greater, 30% by mass or greater, or 40% by mass or greater.

The content of the anti-aging agent in the anti-aging composition may be in a range of 0.01% to 50% by mass, in a range of 0.01% to 30% by mass, in a range of 0.01% to 20% by mass, in a range of 0.1% to 10% by mass, in a range of 0.1% to 5% by mass, in a range of 0.1% to 3% by mass, in a range of 0.3% to 2% by mass, or in a range of 0.6% to 1.5% by mass.

In a case where one kind of inositol derivative is used alone, the content of the anti-aging agent indicates the content of the compound. Further, in a case where a combination of two or more kinds of inositol derivatives is used, the content of the anti-aging agent indicates the total content of these compounds. In a case where the content of the anti-aging agent in the anti-aging composition is in the above-described range, the anti-aging effects (effects of preventing and improving both epidermal wrinkles and dermal wrinkles) tend to be sufficiently obtained.

A method of administering the anti-aging agent or the anti-aging composition is not particularly limited and may be determined depending on the symptoms, the weight, the age, the sex, and the like of a patient. For example, a tablet, a coated tablet, a pill, powder, a granule, a capsule, a liquid, a suspension, and an emulsion are orally administered. Further, an injection is intravenously administered alone or by being mixed with a typical replenisher solution such as glucose or amino acid or intraarterially, intramuscularly, intradermally, subcutaneously, or intraperitoneally administered as necessary. A suppository is intrarectally administered. The skin external agent is applied, attached, or sprayed to the affected area.

The dose of the anti-aging agent or the anti-aging composition cannot be unconditionally determined because the dose thereof varies depending on the symptoms, the weight, the age, the sex, and the like of a patient. In a case of the oral administration, for example, 0.01 to 500 mg of the active component (inositol derivative) per dosage unit form may be administered. Further, in a case of the injection, for example, 0.02 to 250 mg of the active component per dosage unit form may be administered. Further, in a case of the suppository, for example, 0.01 to 500 mg of the active component per dosage unit form may be administered. Further, in a case of the skin external agent, for example, 0.15 to 500 mg of the active component per dosage unit form may be administered.

In addition, the dose per day of the anti-aging agent or the anti-aging composition cannot be unconditionally determined because the dosage thereof varies depending on the symptoms, the weight, the age, the sex, and the like of a patient. For example, 0.005 to 5000 mg of the active component for an adult per day may be administered in one dose or by being divided into one to three doses per day.

Other Embodiments

According to an embodiment of the present invention, there is provided a method of preventing or treating wrinkles on the skin, comprising a step of administering an inositol derivative in which a monosaccharide or an oligosaccharide is bonded to inositol, in which the total amount of the monosaccharide or the oligosaccharide bonded to one inositol molecule is 2 or greater in terms of monosaccharide unit, to a mammal.

According to an embodiment of the present invention, there is provided a method of promoting production of collagen or elastin, comprising a step of administering an inositol derivative in which a monosaccharide or an oligosaccharide is bonded to inositol, in which the total amount of the monosaccharide or the oligosaccharide bonded to one inositol molecule is 2 or greater in terms of monosaccharide unit, to a mammal.

According to an embodiment of the present invention, there is provided an inositol derivative used for treating wrinkles on the skin in which a monosaccharide or an oligosaccharide is bonded to inositol, in which the total amount of the monosaccharide or the oligosaccharide bonded to one inositol molecule is 2 or greater in terms of monosaccharide unit.

According to an embodiment of the present invention, there is provided an inositol derivative used for promoting production of collagen or elastin in which a monosaccharide or an oligosaccharide is bonded to inositol, in which the total amount of the monosaccharide or the oligosaccharide bonded to one inositol molecule is 2 or greater in terms of monosaccharide unit.

According to an embodiment of the present invention, there is provided a use of an inositol derivative in which a monosaccharide or an oligosaccharide is bonded to inositol, in which the total amount of the monosaccharide or the oligosaccharide bonded to one inositol molecule is 2 or greater in terms of monosaccharide unit, for producing an anti-aging agent.

According to an embodiment of the present invention, there is provided a use of an inositol derivative in which a monosaccharide or an oligosaccharide is bonded to inositol, in which the total amount of the monosaccharide or the oligosaccharide bonded to one inositol molecule is 2 or greater in terms of monosaccharide unit, for producing a collagen production promotor or an elastin production promotor.

EXAMPLES

Hereinafter, the present invention will be described in more detail with reference to examples, but the present invention is not limited to the following examples.

Example 1

Preparation of Inositol Derivative

Each inositol derivative of Examples 1 to 6 and Comparative Example 1 was prepared by bonding glucose or a saccharide having glucose as a monosaccharide unit to myo-inositol. Each inositol derivative was analyzed according to liquid chromatography mass spectrometry (LC-MS), and the proportion of the molecule in which the number of glucoses bonded to myo-inositol was 1, 2, 3, or 4 or more was listed in Table 1, on a % by mass basis. Further, in the inositol derivative of Example 2, the proportion of the molecule in which the number of glucoses of the glucose chain bonded to myo-inositol was 1 was 12% by mass, the proportion of the molecule in which the number of glucoses of the glucose chain bonded to myo-inositol was 2 was 30% by mass, the proportion of the molecule in which the number of glucoses of the glucose chain bonded to myo-inositol was 3 was 9% by mass, the proportion of the molecule in which the number of glucoses of the glucose chain bonded to myo-inositol was 4 was 12% by mass, and the proportion of the molecule in which the number of glucoses of the glucose chain bonded to myo-inositol was 5 was 2% by mass.

TABLE 1

| Number of glucoses (% by mass) | Example 1 | Example 2 | Example 3 | Example 4 | Example 5 | Example 6 | Comparative Example 1 |
|---|---|---|---|---|---|---|---|
| 1 | 38 | 12 | 21 | 3 | 0 | 0 | 100 |
| 2 | 28 | 30 | 37 | 32 | 1 | 0 | 0 |
| 3 | 10 | 9 | 18 | 42 | 12 | 16 | 0 |
| 4 or more | 5 | 14 | 24 | 23 | 87 | 84 | 0 |

Example 2

Examination of Effects of Promoting Expression of Collagen or Elastin in Fibroblasts The gene expression of collagen and elastin in normal human fibroblasts was examined. Further, it has been known that a decrease in expression level of collagen and elastin due to cellular aging causes wrinkles.

NB1RGB cells (purchased from Riken BioResource Center), which are normal human fibroblasts, were seeded in a plastic dish at a seeding density of 10000 cells/cm$^2$ and cultured in Dulbecco's Modified Eagle's medium (DMEM) (manufactured by Sigma-Aldrich Corporation) containing 10% fetal bovine serum for 24 hours. Thereafter, each inositol derivative of Examples 1 to 6 and Comparative Example 1 in a state of being dissolved in purified water was added to the medium at a final concentration of 0.01 w/v % and further cultured for 24 hours. As a control, NB1RGB cells obtained by adding the same volume of purified water in place of 0.01 w/v % of the inositol derivative to a medium were cultured in the same manner as described above. Further, for comparison, NB1RGB cells obtained by adding 0.001 w/v % of myo-inositol in a state of being dissolved in purified water in place of the inositol derivative to a medium were cultured in the same manner as described above.

Next, total RNA was extracted from cells of each group to synthesize cDNA. Next, the expression levels of collagen genes and elastin genes in NB1RGB cells of each group were quantified by performing quantitative real-time PCR using the cDNA as a template. Further, the expression level of glyceraldehyde-3-phosphate dehydrogenase (GAPDH), which is a housekeeping gene, was quantified as an internal standard gene, and the expression levels of collagen genes and elastin genes were respectively standardized based on the expression level of the GAPDH genes in the NB1RGB cells of each group.

As a primer for amplifying the GAPDH genes, GAPDH primer (ID: HA067812) (manufactured by Takara Bio Inc.) was used. Further, as a primer for amplifying the collagen genes, COLA1 primer (ID: HA181838) (manufactured by Takara Bio Inc.) was used. Further, as a primer for amplifying the elastin genes, ELA primer (ID: CH000581) (manufactured by Takara Bio Inc.) was used.

The standardized expression levels of collagen and elastin genes are listed in Table 2. In the inositol derivatives of Examples 1 to 6, the effect of promoting expression of collagen genes and elastin genes was remarkable compared to the purified water as a control. Further, in the myo-inositol and the inositol derivative of Comparative Example 1, a decrease in expression of collagen genes was shown compared to the purified water as a control. On the contrary, in the inositol derivatives of Examples 1 to 6, the expression of collagen genes was promoted.

TABLE 2

| Sample | Expression level of genes (relative value) | |
|---|---|---|
|  | Collagen | Elastin |
| Purified water | 1.00 | 1.00 |
| myo-Inositol | 0.54 | 1.23 |
| Comparative Example 1 | 0.69 | 1.33 |
| Example 1 | 1.13 | 1.23 |
| Example 2 | 1.29 | 1.64 |
| Example 3 | 1.15 | 1.45 |
| Example 4 | 1.28 | 1.52 |
| Example 5 | 1.25 | 1.57 |
| Example 6 | 1.18 | 1.46 |

Example 3

Preparation of Anti-Aging Composition

Anti-aging compositions (lotions) of Examples 7 and 8 were prepared according to a method of the related art with the compositions listed in Table 3. The above-described inositol derivative of Example 2 was used as the inositol derivative.

TABLE 3

| Lotion | | |
|---|---|---|
| Composition | Example 7 (% by mass) | Example 8 (% by mass) |
| Inositol derivative | 3.0 | 8.0 |
| Water | 86.4 | 80.6 |
| Dipotassium glycyrrhizinate | 0.2 | 0.2 |
| Sodium hyaluronate (1%) | 4.0 | 4.0 |
| Citric acid (10% aqueous solution) | 0.1 | — |
| Sodium citrate | 0.1 | 3.0 |
| Tetrasodim ethylenediaminetetraacetate | 0.1 | 0.1 |
| Glycerin | 4.0 | 4.0 |
| Ethanol | 2.0 | — |
| Methylparaben | 0.1 | 0.1 |
| Total amount | 100.0 | 100.0 |

Next, an anti-aging composition (gel cream) of Example 9 was prepared according to a method of the related art with the composition listed in Table 4. The above-described inositol derivative of Example 2 was used as the inositol derivative.

TABLE 4

| Gel cream | |
|---|---|
| Composition | Example 9 (% by mass) |
| Hardened rapeseed oil alcohol | 4.2 |
| Isononyl isononanoate | 6.0 |
| Squalene | 9.6 |
| Octyldodecyl myristate | 4.8 |
| Polyglyceryl-10 monostearate | 2.0 |
| Glyceryl stearate | 1.0 |
| α-Tocopherol | 0.2 |
| Methylparaben | 0.1 |
| Propylparaben | 0.05 |
| Xanthan gum | 0.1 |
| 1,3-Butylene glycol | 4.8 |
| Concentrated glycerin | 4.8 |
| Inositol derivative | 2.0 |
| Trisodium citrate | 0.4 |
| water | 59.95 |
| Total amount | 100.0 |

Next, anti-aging compositions (emulsions) of Examples 10 and 11 and Comparative Examples 2 and 3 were prepared according to a method of the related art with the compositions listed in Table 5. The above-described inositol derivative of Example 2 was used as the inositol derivative.

TABLE 5

| Emulsion | | | | |
|---|---|---|---|---|
| Composition | Example 10 (% by mass) | Example 11 (% by mass) | Comparative Example 2 (% by mass) | Comparative Example 3 (% by mass) |
| Inositol derivative | 0.5 | 1.0 | 0.0 | 0.0 |
| myo-Inositol | 0.0 | 0.0 | 0.0 | 1.0 |
| Concentrated glycerin | 5.0 | 5.0 | 5.0 | 5.0 |
| Dipropylene glycol | 3.0 | 3.0 | 3.0 | 3.0 |
| Pentylene glycol | 2.0 | 2.0 | 2.0 | 2.0 |
| Cetearyl alcohol | 1.0 | 1.0 | 1.0 | 1.0 |
| Glyceryl stearate | 3.0 | 3.0 | 3.0 | 3.0 |
| Squalene | 5.0 | 5.0 | 5.0 | 5.0 |
| Cyclomethicone | 2.0 | 2.0 | 2.0 | 2.0 |
| Trioctanoin | 1.0 | 1.0 | 1.0 | 1.0 |
| Ethylhexyl palmitate | 1.5 | 1.5 | 1.5 | 1.5 |
| Carbomer | 0.2 | 0.2 | 0.2 | 0.2 |
| Methylparaben | 0.2 | 0.2 | 0.2 | 0.2 |
| Arginine | 0.2 | 0.2 | 0.2 | 0.2 |
| Water | 75.4 | 74.9 | 75.9 | 74.9 |
| Total amount | 100.0 | 100.0 | 100.0 | 100.0 |

Example 4

Evaluation of Anti-Aging Composition

An area of 1.5 cm×1.5 cm was set on an arm of each of the volunteer subjects, which were 32 healthy adult men and women from whom consent was obtained. The anti-aging compositions of Examples 7 to 11 and Comparative Examples 2 and 3 respectively with a size of a rice grain were applied to the areas twice a day for 28 days.

Further, the above-described subjects were divided into four groups respectively consisting of 8 people, and the emulsions of Examples 10 and 11 and Comparative Examples 2 and 3 were respectively applied to the faces of each group twice a day for 28 days.

(Examination of Transepidermal Moisture Transpiration Amount)

In the morning on the second day after final application of the anti-aging compositions of Examples 7 to 11 and Comparative Examples 2 and 3 to the arms of the subjects, the transepidermal moisture transpiration amount (transepidermal water loss (TEWL) value) in the application areas and non-application areas of the anti-aging compositions in the arms of the subjects were respectively measured using a moisture transpiration amount measuring device (model "VAPOSCAN AS-VT 100RS", manufactured by Asahi Techno Lab).

The measurement results of the TEWL values are listed in Table 6. As a result, the TEWL values in the application areas of the anti-aging compositions of Examples 7 to 11 were significantly lower than the TEWL values in the application areas of the anti-aging compositions of Comparative Examples 2 and 3 and the TEWL values in the non-application areas. Based on the results, it became evident that the anti-aging compositions of Examples 7 to 11 improved the skin moisturizing ability.

were recognized in the groups using the emulsions of Examples 10 and 11 compared to the groups using the emulsions of Comparative Examples 2 and 3. Further, skin and eye troubles did not occur at all during the test period, and it was shown that the emulsions of Examples 10 and 11 did not have safety issues.

TABLE 8

| | Effective in improving wrinkles | |
|---|---|---|
| | cheeks | Outer corners of eyes |
| Example 10 | 6 | 3 |
| Example 11 | 7 | 5 |
| Comparative Example 2 | 2 | 0 |
| Comparative Example 3 | 3 | 2 |

TABLE 6

| | Example 7 | Example 8 | Example 9 | Example 10 | Example 11 | Comparative Example 2 | Comparative Example 3 | Non-application area |
|---|---|---|---|---|---|---|---|---|
| Transepidermal moisture transpiration amount [g/(h · m$^2$)] | 9.5 | 8.6 | 7.9 | 8.5 | 6.6 | 10.9 | 11.1 | 15.3 |

(Examination of Effects of Improving Wrinkles)

After final application of the emulsions of Examples 10 and 11 and Comparative Examples 2 and 3 to the faces of the subjects, the effects of improving wrinkles were evaluated based on the evaluation criteria listed in Table 7. Epidermal fine wrinkles on the cheeks and dermal wrinkles at the outer corners of the eyes were evaluated.

TABLE 7

| Evaluation points | Evaluation criteria |
|---|---|
| 1 | The wrinkles on the cheeks and at the outer corners of the eyes were shallow and not noticeable. |
| 2 | The wrinkles on the cheeks and at the outer corners of the eyes were slightly noticeable when observed closely. |
| 3 | The wrinkles on the cheeks and at the outer corners of the eyes were slightly deep and noticeable. |
| 4 | The wrinkles on the cheeks and at the outer corners of the eyes were apparently deep and noticeable. |

Next, the effects of improving wrinkles on the cheeks and at the outer corners of the eyes using the emulsions of Examples 10 and 11 and Comparative Examples 2 and 3 were collected. A case where a difference between evaluation points before starting the use of the emulsion and evaluation points after the emulsion was applied for one month is 2 points or more was evaluated as "effective"; a case where the difference therebetween was 1 point was evaluated as "slightly effective"; and a case where the difference therebetween was 0 point was evaluated as "ineffective". The number of subjects with the results of "effective" or "slightly effective" was collected as "effective in improving wrinkles".

The results are listed in Table 8. The effects of improving wrinkles on the cheeks and at the outer corners of the eyes

INDUSTRIAL APPLICABILITY

According to the present invention, it is possible to provide an anti-aging agent for skin that exerts effects on both epidermal wrinkles and dermal wrinkles.

The invention claimed is:

1. An anti-aging composition for skin comprising one or more inositol derivatives in which glucose or an oligosaccharide comprising glucose as a constituent unit is bonded to inositol, and a total amount of the glucose or the oligosaccharide bonded to one inositol molecule is 1 or greater in terms of monosaccharide unit,
wherein the one or more inositol derivatives comprises, as an active component, at least one inositol derivative in which glucose or an oligosaccharide comprising glucose as a constituent unit is bonded to inositol, and a total amount of the glucose or the oligosaccharide bonded to one inositol molecule is 2 or greater in terms of monosaccharide unit,
a proportion of the active component among all of said one or more inositol derivatives contained in the anti-aging composition being 79% by mass or greater.

2. The anti-aging composition for skin according to claim 1, wherein the inositol is myo-inositol.

3. The anti-aging composition for skin according to claim 1, further comprising a pharmaceutically acceptable carrier.

4. The anti-aging composition for skin according to claim 1, wherein the proportion of the active component among all inositol derivatives contained in the anti-aging composition is 97% by mass or greater.

5. The anti-aging composition for skin according to claim 1, wherein the proportion of the active component among all inositol derivatives contained in the anti-aging composition is 100% by mass.

6. The anti-aging composition for skin according to claim 1, comprising an inositol derivative in which glucose or an oligosaccharide comprising glucose as a constituent unit is bonded to inositol and in which a total amount of the glucose or the oligosaccharide bonded to one inositol molecule in terms of monosaccharide unit is 4 or greater, and wherein a proportion of the inositol derivative in which glucose or an oligosaccharide comprising glucose as a constituent unit is bonded to inositol and in which a total amount of the glucose or the oligosaccharide bonded to one inositol molecule in terms of monosaccharide unit is 4 or greater among all inositol derivatives contained in the anti-aging composition is 23% by mass to 87% by mass.

7. A method of promoting expression of collagen genes or elastin genes in human fibroblast, comprising administering an effective amount of the anti-aging composition according to claim 1 to a human subject.

8. A method of suppressing a decrease in collagen or elastin in the skin dermis due to aging, comprising administering an effective amount of the anti-aging composition according to claim 1 to a human subject.

\* \* \* \* \*